United States Patent [19]

Libman et al.

[11] 4,046,138
[45] Sept. 6, 1977

[54] DIAGNOSTIC DEVICE FOR LIQUID SAMPLES

[75] Inventors: Gary Libman, Des Plaines; William J. Binard, McHenry; Harish A. Patel, Oak Park, all of Ill.

[73] Assignee: The Kendall Company, Boston, Mass.

[21] Appl. No.: 660,529

[22] Filed: Feb. 23, 1976

Related U.S. Application Data

[63] Continuation of Ser. No. 495,977, Aug. 29, 1974, abandoned.

[51] Int. Cl.² ............................................. A61B 10/00
[52] U.S. Cl. .............................. 128/2 F; 128/DIG. 5; 128/292; 128/295; 73/421 R; 4/110; 195/103.5 R
[58] Field of Search ................ 128/2 F, 2 G, DIG. 5, 128/272, 275, 276, 278, 294, 295; 73/421 R; 4/110; 195/103.5 R, 139

[56] References Cited

U.S. PATENT DOCUMENTS

| 2,992,974 | 7/1961 | Belcove et al. | 195/139 |
| 3,248,302 | 4/1966 | Mackin | 195/139 |
| 3,776,818 | 12/1973 | Khan | 195/139 |
| 3,838,013 | 9/1974 | Bergeron | 195/139 |

Primary Examiner—Robert W. Michell
Assistant Examiner—Henry J. Recla
Attorney, Agent, or Firm—Powell L. Sprunger

[57] ABSTRACT

The present invention is concerned with a diagnostic device for collection of body fluids which is especially convenient for taking mid-stream urine specimens. Generally the device comprises a bipartible receptacle having a removable portion which contains a bacteriological medium. The removable portion may be incubated and analyzed subsequent to substantially immediate inoculation of the medium with any pathogens present in the fluid.

2 Claims, 6 Drawing Figures

DIAGNOSTIC DEVICE FOR LIQUID SAMPLES

This is a continuation of application Ser. No. 495,977 filed Aug. 29, 1974 now abandoned.

BACKGROUND OF THE INVENTION

This invention relates to the detection of the presence of, and type of, bacteria in body fluids (human and animal), which is an ever-constant problem for the medical profession both for diagnostic and treatment reasons. Unreliability of laboratory tests is not uncommon. Often a time lag is present between collection of the body fluid to be tested and the inoculation of a culture medium therewith. Some microorganisms multiply so rapidly that such a time lag makes the distinction between a significant infection and an overgrowth of contaminants impossible. Other microorganisms are so sensitive to their environment that they may not survive a time lag and a delay in inoculation of culture media will not present a true picture for the diagnostician. Any apparatus and/or procedure that will eliminate or shorten the time lag will greatly help laboratory analysts.

One of the major problems confronting hospitals today is the accurate detection of urinary tract infections. The presence of bacteria in urine is termed bacteriuria. Clean voided urine from normal individuals generally contains microorganisms that are indigenous residents of the urethra. Urine in the bladder is ordinarily sterile. The presence of any bacteria in the bladder or upper urinary tract is considered abnormal. Significant bacteriuria is a term for describing the numbers of bacteria in voided urine that exceed the numbers usually due to contamination from the anterior urethra. Inasmuch as voided urine is an ideal growth medium for microorganisms, it is imperative that an accurate assessment of bacteriuria be made immediately after a specimen is voided. Prior art techniques for bacterial culturing have disadvantages over our invention in that each has one or more of the following drawbacks: difficulty of interpretation or quantitation, difficulty of performance, excessive expense and time consumption, significant delay between collection of the sample and inoculation of the medium.

An advantage of our invention is that with an embodiment of our device a patient may void directly into the collection device, yet the culture medium may be substantially immediately inoculated with that specimen, by the patient, if desired.

Our invention also allows subculturing of bacterial colonies for further biochemical studies. This is difficult with many of the prior art culturing devices.

Our invention avoids the difficulties of interpretation and collection in the test tubes containing agar which have been used.

With regard to the detection of gonorrhea from a urine sample, it has been necessary in the past to centrifuge the sample to precipitate the heavier bacterial material from the liquid, including the *Neisseria gonorrhoeae* bacteria, if present, for inoculating a culture medium. An advantage of our invention is that we are able to culture a urine sample for detection of *N. gonorrhoeae* without having to centrifuge the urine sample.

BRIEF SUMMARY OF THE INVENTION

The principal feature of the present invention is the provision of an apparatus for collecting body fluids, particularly the mid-stream collecting of urine, in a simplified manner which provides for the substantially immediate inoculation of a bacteriological medium by the fluid.

A further feature of our invention is the provision of a method for inoculating a bacterial medium with a body fluid substantially immediately after the fluid leaves the body.

The device of the present invention includes a container having a portion or section thereof retaining a culture medium. The container includes a chamber adapted to receive a liquid sample without contact of the medium with the sample. It is important that the fluid not be collected directly on the medium to prevent damage to the medium, such as the breaking up thereof. Preferably the container is adapted to receive a direct urine discharge. More particularly, our preferred device is bipartible and includes a fluid receptacle and a first close fitting lid therefor and removable therefrom having disposed on the underside thereof a bacteriological medium. After inoculation of the medium with the fluid, a cover can be placed on the removed lid to form an "incubation package". If desired, a second close fitting lid can be placed over the fluid at this point and the fluid therein further analyzed. Alternatively, it is feasible that the receptacle and lid therefor can remain intact, with provision made for discard of fluid in excess of that which is required to inoculate the medium and this, then, forms the "incubation package".

In the method of our invention a liquid sample is directed into a container having a section containing a culture medium. This is done without contacting the medium with the incoming sample so as to avoid damage to the medium and the container is thereafter inverted to inoculate the medium retained in the container with the sample received in the container.

A feature of the invention is that it is especially suitable in obtaining a urine specimen from the mid-stream of micturition, after the urethra has been flushed by a flow from the bladder.

Another feature of the invention is that the device allows substantially immediate and direct inoculation of a bacteriological medium with fluid suspected of containing pathogens.

Yet another feature of the invention is that the diagnostic device accomplishes collection of fluid, inoculation of culture medium, and furnishes an apparatus for incubation.

Still another feature is that the device employs bacteriological media surfaces that allow easy interpretation of diagnostic results and easy subculturing for biochemical evaluation, and the positioning, if desired, of selective and non-selective agars adjacent to one another for ease in presumptive identification.

A further feature of the invention is that the media can be incubated in a horizontal position, which is more reliable than vertical incubation found in many commercial products.

Also a feature of the invention is that its use shows an excellent correlation with standard techniques in enumeration and in presumptive identification of organisms.

Yet a further feature of the invention is the ability to culture a urine sample for detection of *Neisseria gonorrhoeae* bacteria without having to centrifuge the sample.

Another feature is the ability to culture a urine sample for the detection of yeast infections.

Further features will become readily apparent from the appended claims and from the following description

DESCRIPTION OF THE PREFERRED EMBODIMENTS

Figure 1:
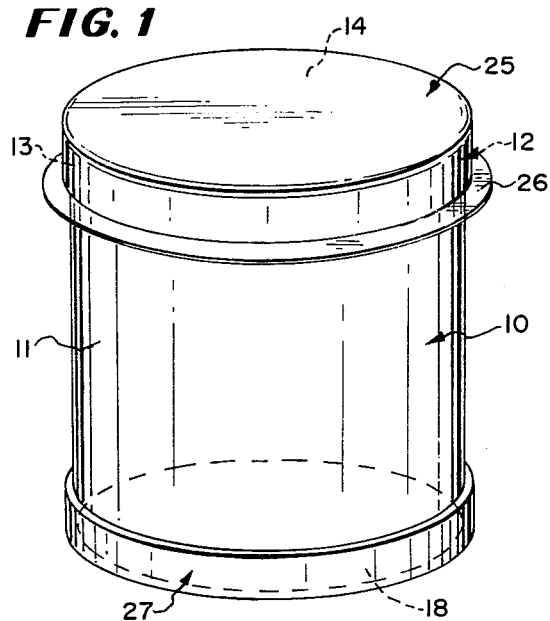
FIG. 1 is an isometric view of the collection and inoculation apparatus of the present invention.
Figure 2:
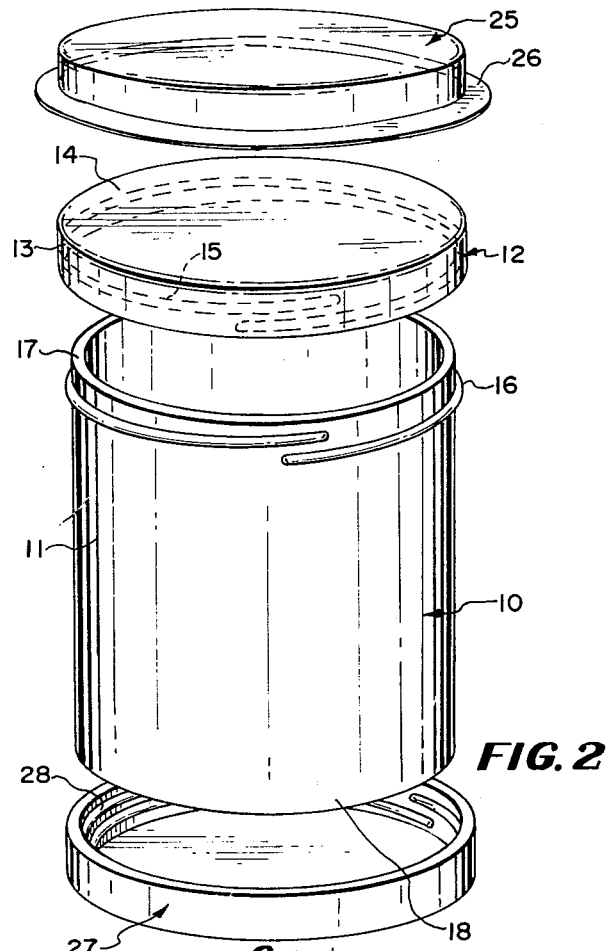
FIG. 2 is an exploded view of the embodiment of FIG. 1, showing the inoculation lid or cap of the apparatus removed from the upper portion of the body of the collection apparatus, the cover for the inoculation lid removed and the second lid removed from the lower portion of the body of the collection apparatus.

Referring now to FIGS. 1 and 2, a collection and inoculation device generally 10 comprises receptacle 11 and a first, inoculation, lid, generally 12, having a top portion 14. The rim 13 of lid 12 may be internally threaded, as shown in FIG. 2 at 15, to mesh with threads 16 annularly disposed around the upper end 17 of receptacle 11. Cover, generally 25, may be conveniently removably affixed to device 10 as by fitting over lid 12. A second, closure, lid, generally 27, may be conveniently removably affixed to receptacle 11 as by frictionally fitting about the bottom 18 thereof. Preferably lid 27 is internally threaded as shown in FIG. 2 at 28 to mesh, when and if desired, with threads 16. The device is fabricated of conventional materials, i.e. metal, glass, plastic, etc. It is, of course, necessary that the material used for the manufacture of the device not react chemically with the body fluid being collected. Preferably the device is transparent. We prefer to use a rigid plastic for the receptacle, with the lid or lids of plastic or metal. The cover for the device is preferably made of a transparent plastic with a low moisture permeability rate.

Figure 3:
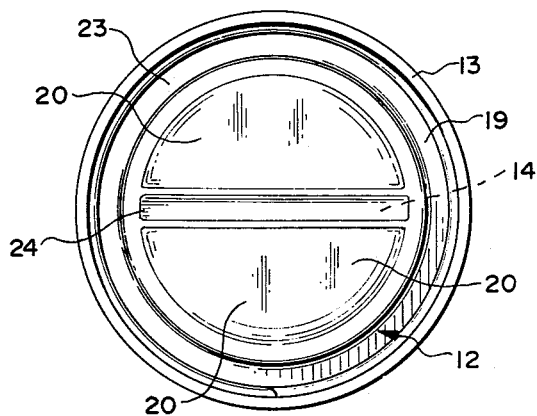
FIG. 3 is an inner bottom view of the inoculation lid or cap of FIGS. 1 and 2, showing the bacteriological media therein.
Figure 4:
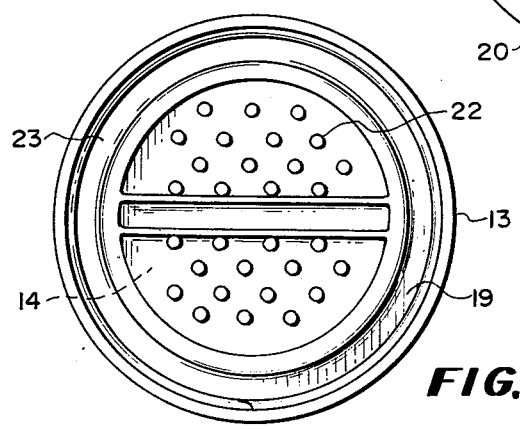
FIG. 4 is an inner bottom view of the inoculation lid or cap of FIGS. 1 and 2 without the media and showing the means for securing the media in the lid.

As illustrated in FIG. 3, inoculation lid 12 has affixed to the inner top surface 19 thereof a bacteriological medium 20. This is conveniently done as by placing the media onto prongs 22, shown in FIG. 4. If more than a single culture medium is employed, we have found it is preferable to physically separate the media within the inner top surface, in order to avoid adulteration, such as by leaving spacer 24 between them. While FIG. 3 shows media 20 in two semicircular configurations, any convenient configuration of media if feasible so long as an annular area 23 is left around the circumference of the lid sufficiently wide to receive the upper end 17 of receptacle 11 and allow the lid to be securely fastened to receptacle 11.

Preferably we use two or more different media, selective and nonselective, adjacent to one another, thereby achieving the important feature of presumptive identification of pathogens in a single culturing. The preferred agars we use are CLED agar and MacConkey Agar or EMB Agar. CLED agar (Cystine Lactose Electrolyte Deficient Agar) is ideal in enumerating and presumptively identifying urinary flora. It supports growth of urinary pathogens and contaminants. Additionally, the lack of electrolytes prevents a common culturing problem—swarming of Proteus. Organisms can be presumptively identified by color of colonies and media and/or morphology of colonies. MacConkey Agar and EMB Agar are well-known differential media for detection and isolation of enteric microorganisms. MacConkey and EMB agars have been used in hospitals for many years. The common gram negative organisms (responsible for more than 90% of uninary tract infections) can be identified readily with MacConkey Agar and EMB Agar.

Figure 6:
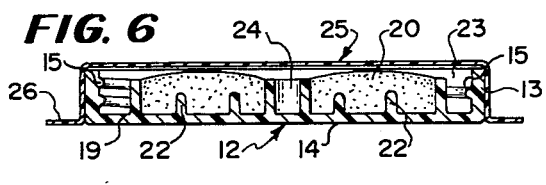
FIG. 6 is a cross-section of the view of FIG. 5, taken along the line 6—6 thereof.
Figure 5:
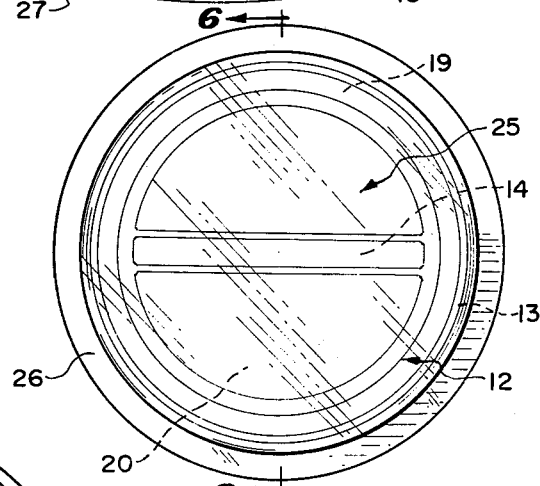
FIG. 5 shows a cover in place on the inoculation lid of the view of FIG. 3, forming the "incubation package" of the invention.

FIGS. 5 and 6 show the incubation package wherein rim 13 and the inner lid 19 containing bacteriological medium is enclosed by cover 25 fitting snugly thereover. Cover 25 includes a flange portion 26 for ease in seating and unseating cover 25 in an aseptic manner, thus not complicating the diagnostic results.

In operation, assuming collection of urine is desired, device 10 is given to a person from whom it is desired to obtain a urine specimen. Receptacle 11 is preferably of a size to allow urine to be voided directly therein. A doctor or technician advises the person regarding when the specimen is to be collected, i.e. first emmission urine, mid-stream, etc. The person from whom the specimen is to be received removes the lid 12 from the bipartible device. After lid 12 has been removed, the urine is collected in receptacle 11 and lid 12 is replaced on the receptacle. Device 10 is then inverted sufficiently to let the liquid contact the media for a brief period of time to allow for an aliquot amount to be absorbed onto the surface. After inoculation the device is returned to its upright position, the lid 12 is again removed and cover 25 therefor is grasped by its flange edge 26 to unseat it from its waiting position and placed over the underside 19 of lid 12. Thus cover 25 and lid, generally 12, provide a package ready to be incubated in the preferred horizontal position. Any excess fluid can be discarded from receptacle 11 or, if desired, may be sealed with second, closure, lid 27, and used for further analysis.

If it is desired to culture the urine for the microorganism *Neisseria gonorrhoeae* we have found that it is feasible to circumvent centrifuging by using a receptacle of sufficient volume to allow settling out of the microorganism onto the media when the device is tilted or inverted for on the order of at least about 2 minutes, with inoculation taking usually not more than 10 minutes. When it is desired to culture for this microorganism, the agar employed is a standard gonococcal medium. i.e. Transgrow or Thayer-Martin.

It is seen that with the use of our invention no time lag occurs between sampling and inoculating of bacterial culture media and an incubation package is provided that is exceptional with regard to providing identification of pathogens and ease of subculturing for biochemical evaluation. A system is provided which correlates to a high degree with standard technique in enumeration and presumptive identification of organisms. The ease and simplicity of the technique, together with its reliability, made our invention of particular value to the busy laboratory.

The foregoing disclosure is offered for public dissemination in return for the grant of a patent. Although it is detailed to ensure adequacy and aid understanding, this is not intended to prejudice that purpose of a patent which is to cover each new inventive concept therein no matter how others may later disguise it by variations in form or additions or further improvements.

We claim:

1. A diagnostic device for use with a sample of body fluid, said diagnostic device comprising a four-piece separable container including a cylindrical sidewall and open top and a closed bottom forming a receptacle, a first lid having a first side and a second side detachably secured to the top of said container, a second lid detachably secured to the bottom of said container, a cover detachably secured over the first side of said first lid, said first lid having an inner planar surface having upstanding annular ring and upstanding spaced prongs both extending from said second side for holding a culture medium on said planar surface, said ring being spaced inwardly from the periphery of said lid to provide an annular area around the circumference of said lid to receive the top of said cylindrical sidewall, said first lid being removable from the top of said container in order for the containers to receive the body sample and said container being adapted to be inverted when the first lid is secured to the top of said container to thereby contact said medium with said body sample to inoculate said culture medium, said first lid may be removed from the top of said container and said cover may be placed over the second side of said first lid after inoculation of said culture medium to form an incubation package and said second lid may be removed from the bottom of said container and secured to the top of said container to use said sample for further analysis.

2. The diagnostic device as set forth in claim 1 further characterized in that the first side of said first lid also has a spacer so that said inner planar surface may receive more than a single culture medium.

* * * * *